US007955311B2

(12) United States Patent
Tanaka et al.

(10) Patent No.: US 7,955,311 B2
(45) Date of Patent: Jun. 7, 2011

(54) DISPOSABLE DIAPER WITH STRETCHABLE SUSPENDER MEMBERS JOINED OUTSIDE ABSORBENT PAD

(75) Inventors: Yoshikazu Tanaka, Kagawa-ken (JP); Hirotomo Mukai, Kagawa-ken (JP)

(73) Assignee: Uni-Charm Corporation, Ehime (JP)

( * ) Notice: Subject to any disclaimer, the term of this patent is extended or adjusted under 35 U.S.C. 154(b) by 668 days.

(21) Appl. No.: 10/115,707

(22) Filed: Apr. 4, 2002

(65) Prior Publication Data

US 2002/0147439 A1    Oct. 10, 2002

(30) Foreign Application Priority Data

Apr. 6, 2001   (JP) .................................. 2001-108630

(51) Int. Cl.
 *A61F 13/15*   (2006.01)
(52) U.S. Cl. ............ 604/385.3; 604/385.22; 604/385.26
(58) Field of Classification Search ............. 604/385.03, 604/385.22, 385.27, 385.01, 385.26, 385.3
See application file for complete search history.

(56) References Cited

U.S. PATENT DOCUMENTS

| 4,743,246 | A | * | 5/1988 | Lawson | .................... 604/385.27 |
| 5,575,783 | A | * | 11/1996 | Clear et al. | ............... 604/385.22 |
| 5,858,012 | A | * | 1/1999 | Yamaki et al. | ........... 604/385.27 |
| 6,142,983 | A | | 11/2000 | Suprise et al. | |
| 6,375,646 | B1 | * | 4/2002 | Widlund et al. | ........... 604/385.3 |
| 6,423,045 | B1 | * | 7/2002 | Wise et al. | ................ 604/385.12 |
| 6,551,294 | B1 | * | 4/2003 | Elsberg et al. | ........... 604/385.01 |
| 6,648,868 | B2 | * | 11/2003 | Sayama et al. | ........... 604/385.22 |
| 6,808,516 | B2 | * | 10/2004 | Tsuji et al. | ............... 604/385.25 |
| 2001/0016720 | A1 | * | 8/2001 | Otsubo | ..................... 604/385.22 |
| 2001/0049512 | A1 | * | 12/2001 | Kawamura et al. | ........... 604/312 |
| 2003/0045855 | A1 | * | 3/2003 | Ono et al. | ...................... 604/387 |

FOREIGN PATENT DOCUMENTS

| EP | 0 763 353 | A2 | | 3/1997 |
| EP | 0761194 | A2 | * | 12/1997 |
| EP | 0 904 753 | A2 | | 3/1999 |
| EP | 1 080 708 | A2 | | 3/2001 |
| JP | 11-99165 | | | 4/1999 |

* cited by examiner

*Primary Examiner* — Lynne Anderson
(74) *Attorney, Agent, or Firm* — Brinks Hofer Gilson & Lione

(57) ABSTRACT

A disposable diaper includes a pants member and a body fluid absorbent pad lying inside the pants member. The pad is connected to elastic first and second suspender members extending in a circumferential direction of the diaper and joined under extension in the circumferential direction of the diaper to the pants member. Front and rear ends of the pad are joined to the suspender members in middle zones of these suspender members of which transversely opposite side edges are joined to transversely opposite side edges of front and rear waist regions. Inner and outer ends of the suspender members are joined to the front and rear waist regions in a joining zones arranged intermittently in the circumferential direction of the diaper.

8 Claims, 4 Drawing Sheets

DISPOSABLE DIAPER WITH STRETCHABLE SUSPENDER MEMBERS JOINED OUTSIDE ABSORBENT PAD

BACKGROUND OF THE INVENTION

This invention relates to a disposable diaper adapted to absorb and retain bodily discharges.

Japanese Patent Application No. 1999-99165A discloses a disposable diaper comprising a pants member composed of front and rear waist regions between which a crotch region lies wherein transversely opposite side edge portions of these waist regions are overlaid and joined together to define a waist-hole and a pair of leg-holes, and a body fluid absorbent pad lying inside the pants so as to be centered on the crotch region and to extend into the front and rear waist regions. The pad comprises a liquid-pervious topsheet, a liquid-impervious backsheet and a liquid-absorbent core disposed between these two sheets. The pad lies just above the crotch region and is connected to a pair of belt-like elastic suspender members extending on the front and rear waist regions in a circumferential direction of the waist. These suspender members are connected under extension in the circumferential direction of the waist to the pants member.

In this diaper of prior art, front and rear ends of the pad are joined to the suspender members in circumferentially middle zones of these suspender members. This diaper allows a size of the pad to be minimized and, in addition, is effective to prevent the pants member and the pad from coming in close contact with a wearer's skin over a large area so as to avoid the wearer to suffer from stuffiness.

With the diaper disclosed in the above-cited Application, an intermediate portion of each suspender member extending between its transversely opposite ends is not joined to the pants member, so that this portion of the suspender member is normally free to be spaced from the pants member. Such arrangement may cause the wearer's leg(s) to be caught by the intermediate portion(s) or to be inserted into a space between the pants member and the intermediate portion(s) when it is desired to put the diaper on the wearer's body. In consequence, unexpected time and labor may be taken to wear the diaper.

SUMMARY OF THE INVENTION

It is an object of this invention to provide a disposable diaper improved so that a diaper can be smoothly worn without apprehension that wearer's leg(s) might be caught by suspender member(s) or erroneously inserted into a space between a pants member and the suspender member(s).

According to this invention, there is provided a disposable diaper comprising a pants member having front and rear waist regions and a crotch region, wherein transversely opposite side edge portions of the waist regions are overlaid and joined together so as to define a waist-hole and a pair of leg-holes, and a body fluid absorbent pad lying inside the pants member and extending from the crotch region into the front and rear waist regions, wherein the pad is connected to a pair of elastically stretchable first and second suspender members lying inside the pants member and extending on the front and rear waist regions in a circumferential direction of the waist and the first and second suspender members are joined under extension in the circumferential direction of the diaper to the pants member.

The pad further has front and rear ends extending across middle zones of the front and rear waist regions in the circumferential direction of the pants of the pants member and transversely opposite side edges extending between the front and rear ends while the first and second suspender members respectively have inner ends extending in the circumferential direction of the pants bordering on the crotch region, outer ends extending in the circumferential direction of the diaper in vicinity of the waist-hole and transversely opposite side edges extending in the longitudinal direction between the inner and outer ends, and the front and rear ends of the pad are joined to the first and second suspender members in middle zones thereof as viewed in the circumferential direction of the pants, the side edges of the first and second suspender members are joined to the front and rear waist regions along the side edges thereof as viewed in the circumferential direction of the pants and the outer ends of the first and second suspender members are joined to the front and rear waist regions along joining zones arranged intermittently in the circumferential direction of the diaper.

This invention includes the following embodiments:

The joining zones are formed on the outer ends of the first and second suspender members immediately outside intersections of the front and rear ends of the transversely opposite side edges of the pad.

The plurality of elastic members extending on the front and rear waist regions of the pants member in the circumferential direction of the waist are spaced one from another in the longitudinal direction between the waist-hole and the leg-holes, the first and second suspender members are attached to the front and rear waist regions being under extension in the circumferential direction of the waist, and elastic members extending on the crotch region of the pants member in the circumferential direction of the legs are attached under extension to peripheral edges of the leg-holes.

The elastic members extending in the circumferential direction of the legs are attached under extension to the peripheral edges of the leg-holes.

DETAILED DESCRIPTION OF THE PREFERRED EMBODIMENTS

Details of the disposable diaper according to this invention will be more fully understood from the description given hereunder in reference to the accompanying drawings.

Figure 1:
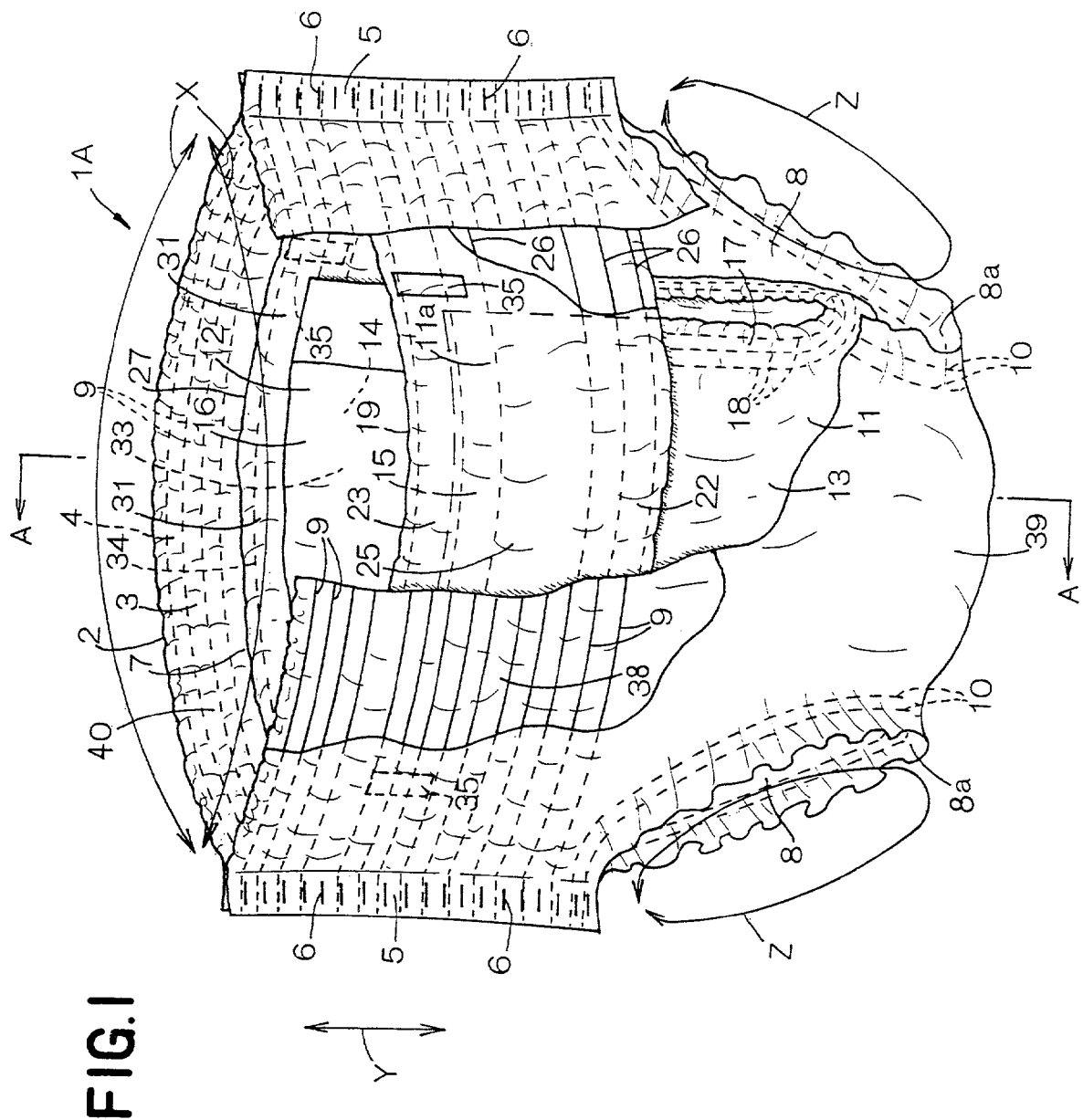
FIG. 1 is a partially cutaway perspective view showing the diaper according to this invention.
Figure 2:
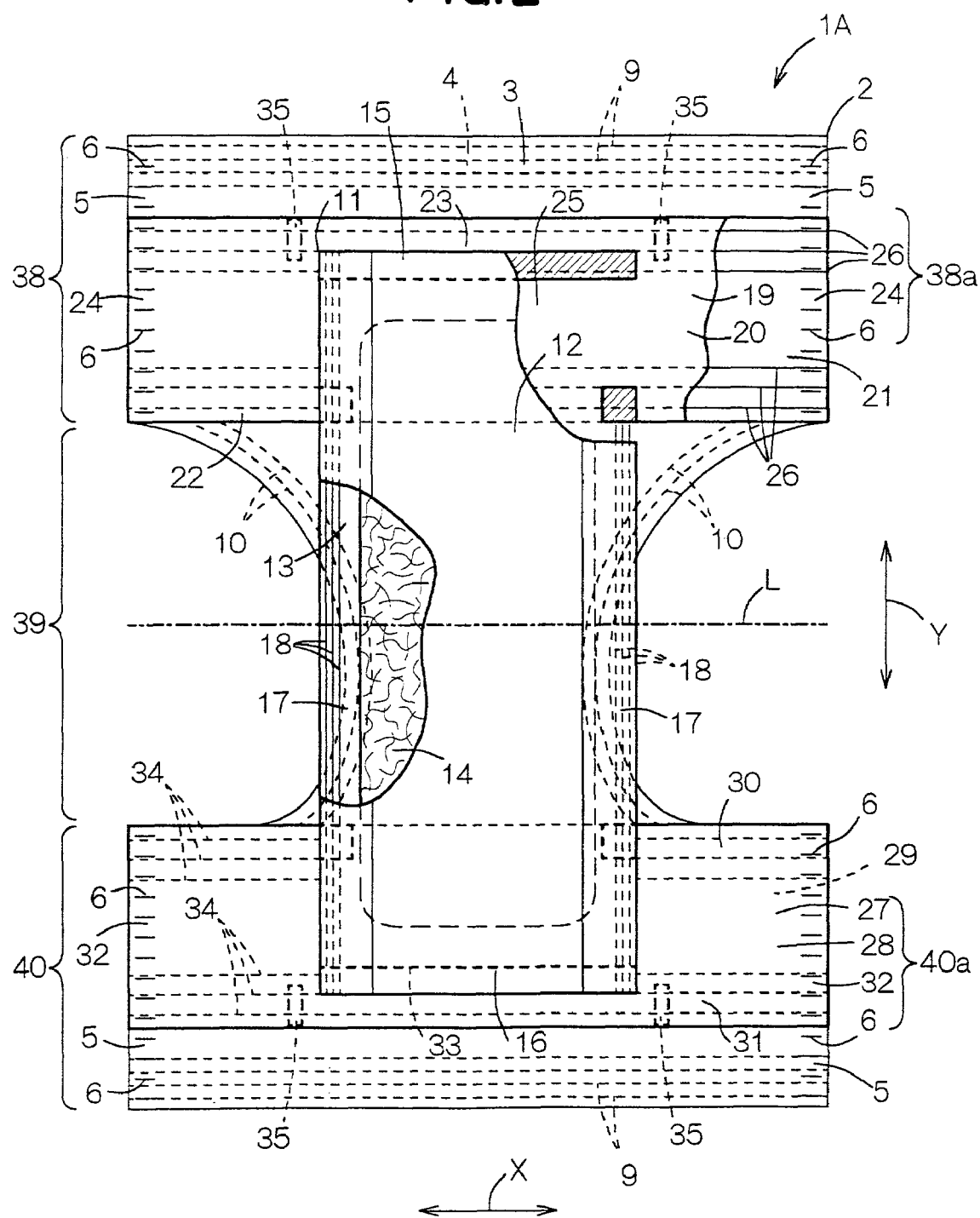
FIG. 2 is a partially cutaway plan view showing the diaper of FIG. 1 as developed.
Figure 3:
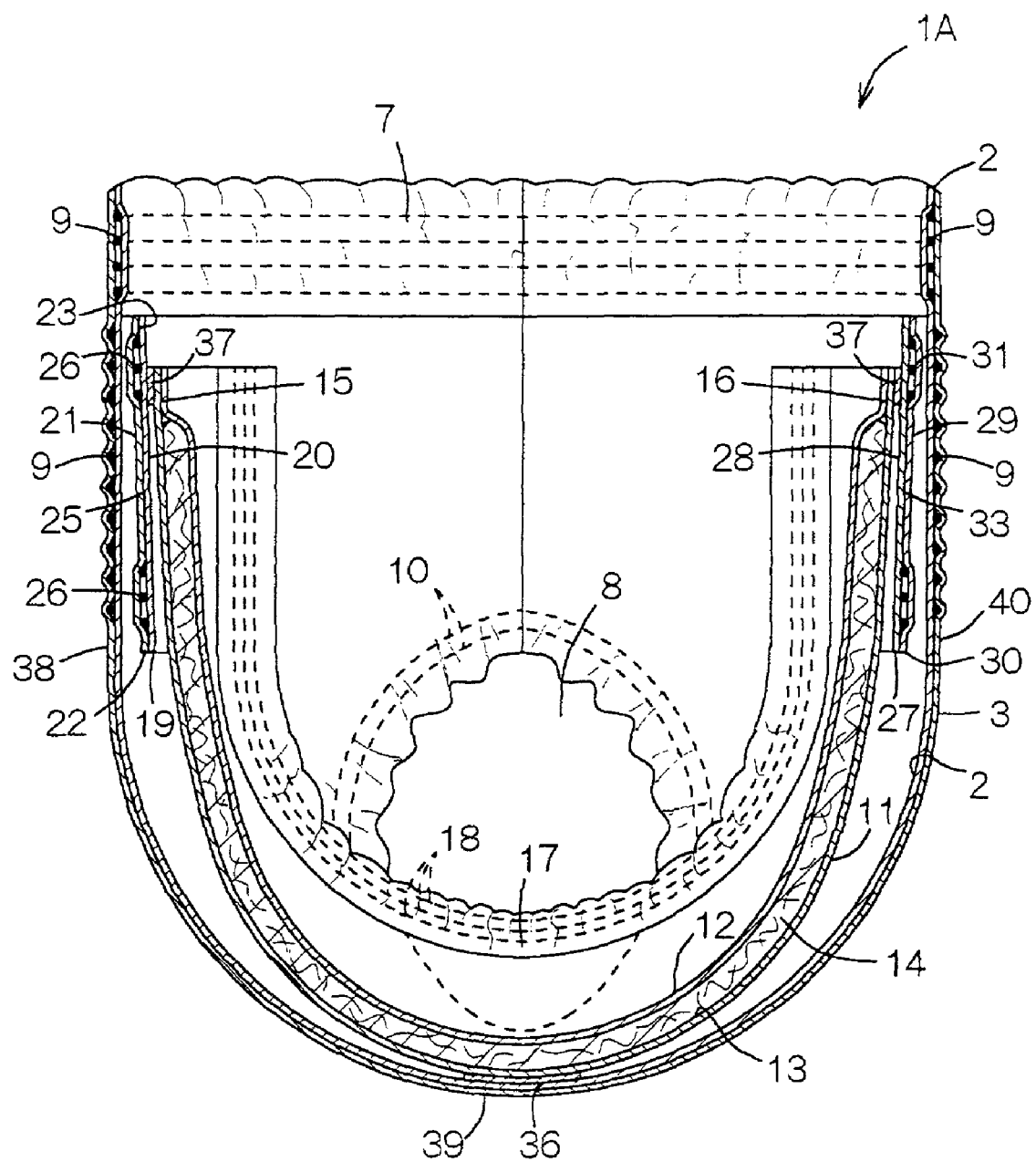
FIG. 3 is a cross-sectional view taken along a line A-A in FIG. 1.

FIG. 1 is a partially cutaway perspective view showing a diaper 1A and FIG. 2 is a plan view showing the diaper 1A in FIG. 1 as developed after its front and rear waist regions 38, 40 have been disconnected from each other and partially cutaway, and FIG. 3 is a cross-sectional view taken along a line A-A in FIG. 1. In FIG. 1, a circumferential direction of the diaper 1A is indicated by an arrow X, a longitudinal direction of the diaper 1A is indicated by an arrow Y, and a circumferential direction of each leg-hole in the diaper 1A is indicated by an arrow Z. In FIG. 2, a transverse direction of the diaper 1A in its developed state is indicated by an arrow X and its longitudinal direction is indicated by an arrow Y. Referring to the plan view of FIG. 2, a pants member 2, a pad 11 and first and second suspender members 19, 27 are under extension in the transverse direction as well as in the longitudinal direction. Inner surfaces of top-and backsheets 12, 13 described herein refer to the surfaces facing a core 14 and outer surfaces of these sheets 12, 13 described herein refer to the surfaces facing away from the core 14.

The diaper 1A comprises the pants member 2, the body fluid absorbent pad 11 lying on an inner side of the pants member 2 and belt-like elastic first and second suspender members 19, 27 lying between the pants member 2 and the pad 11 so as to connect the pants member 2 with the pad 11.

The pants member 2 comprises a pair of substantially liquid-impervious sheets 3, 4 placed upon each other and is hourglass-shaped as viewed in its plan view. The pants member 2 is composed of front waist region 38, a rear waist region 40 opposed to the front waist region 38 and a crotch region 39 interposed between these front and rear waist regions 38, 40. In the pants member 2, transversely opposite side edge portions 5 of the front and rear waist regions 38, 40 extend in the longitudinal direction, are overlaid and joined together by means of plural heat-sealing lines 6 provided intermittently in the longitudinal direction along the side edge portions 5 so as to define a waist-hole 7 and a pair of leg-holes 8.

A plurality of elastic members 9 extend in the circumferential direction of the waist regions 38, 49 and are joined under extension to the front and rear waist regions 38, 40 wherein these elastic members 9 are spaced in a pre-determined distance in the longitudinal direction around the waist-hole 7 and the leg-holes 8. Similarly, ribbon-like elastic member 10 extending in a circumferential direction of the leg-holes are secured under extension to peripheral edges 8a of the respective leg-holes 8. Both the elastic members 9 extending in the circumferential direction of the waist regions and the elastic member 10 associated with the leg-holes 8 are interposed between the sheets 3, 4 constituting the pants member 2 and joined to these sheets 3, 4.

The pad 11 comprises the liquid-pervious topsheet 12 facing the wearer's skin, the liquid-impervious backsheet 13 facing away from the wearer's skin and the liquid-absorbent core 14 disposed between these sheets 12, 13. The core 14 is joined to the inner surface of at least one of the top-and backsheets 12, 13.

The pad 11 lies in the crotch region 39 of the pants member 2 and further extends into the front and rear waist regions 38, 40. The pad 11 has a contour defined by a front end 15 lying in a middle zone 38a of the front waist region 38 and extending in the circumferential direction of the front waist region 38, a rear end 16 lying in a middle zone 40a of the rear waist region 40 and extending in the circumferential direction of the rear waist region 40 and transversely opposite side edges 17 extending in the circumferential direction of the respective legs. The pad 11 is provided along its transversely opposite side edges 17 with a pair of elastic members 18 extending in the circumferential direction of the respective legs and joined under extension to these side edges 17. The elastic members 18 are disposed between the top-and backsheets 12, 13 and joined to the inner surfaces of these sheets 12, 13.

The pad 11 is connected to the crotch region 39 of the pants member 2 and free in the other regions thereof. In the crotch region 39 of the pants member 2, the backsheet 13 comprising the pad 11 has its outer surface joined to the sheet 3 comprising the pants member 2 by means of a hot melt adhesive 36.

The first suspender member 19 is formed by two substantially liquid-impervious sheets 20, 21 placed upon each other extending in the circumferential direction across the front waist region 38 of the pants member 2. The first suspender member 19 has an inner end 22 extending in the circumferential direction of the waist bordering on the crotch region 39, an outer end 23 extending in the circumferential direction of the waist in the vicinity of the waist-hole 7 and transversely opposite side edges 24 extending in the longitudinal direction of the pants member 2 between the inner and outer ends 22, 23. The inner and outer ends 22, 23 of the first suspender member 19 are respectively provided with a plurality of elastic members 26 extending in the circumferential direction of the waist and joined under extension thereto. These elastic members 26 are disposed between the sheets 20, 21 forming the first suspender member 19 and joined to these sheets 20, 21.

The second suspender member 27 is formed by two substantially liquid-impervious sheets 28, 29 placed upon each other extending in the circumferential direction across the rear waist region 40 of the pants member 2. The second suspender member 27 has an inner end 30 extending in the circumferential direction of the waist bordering on the crotch region 39, an outer end 31 extending in the circumferential direction of the waist in the vicinity of the waist-hole 7 and transversely opposite side edges 32 extending in the longitudinal direction of the pants member 2 between the inner and outer ends 30, 31. The inner and outer ends 30, 31 of the second suspender member 27 are respectively provided with a plurality of elastic members 34 extending in the circumferential direction of the waist and joined under extension thereto. These elastic members 34 are disposed between the sheets 28, 29 forming the second suspender member 27 and joined to these sheets 28, 29.

The front end 15 of the pad 11 is joined to the first suspender member 19 by means of a hot melt adhesive 37 in a circumferentially middle zone 25 thereof. The side edges 17 of the pad 11 are joined to the inner end 22 of the first suspender member 19 by means of a hot melt adhesive (not shown). The rear end 16 of the pad 11 is joined to the second suspender member 27 by means of the hot melt adhesive 37 in a circumferentially middle zone 33 thereof. The side edges 17 of the pad 11 are joined to the inner end 30 of the second suspender member 27 by means of a hot melt adhesive (not shown). Along the front and rear ends 15, 16 and the side edges 17 of the pad 11, the outer surface of the backsheet 13 forming the pad 11 is joined to the sheets 20, 28 forming these suspender members 19, 27.

The first and second suspender members 19, 27 are connected under extension in the transverse direction to the pants member 2. The first and second suspender members 19, 27 respectively have the transversely opposite side edges 24, 32 joined to the front and rear waist regions 38, 40 along the side edges 5 of these waist regions 38, 40 by means of the heat-sealing lines 6 and the outer ends 23, 31 joined to the front and rear waist regions 38, 40 in respective pairs of joining zones 35 arranged so as to be spaced from each other in the circumferential direction of the waist. These pairs of joining zones 35 are formed at intersecting points 11a on the respective outer ends 23, 31 of these suspender members 19, 27 immediately outside the points at which the front and rear ends 15, 16 and the side edges 17 of the pad 11 intersect each other. In these joining zones 35, the pants member 2 and the first and second suspender members 19, 27 are joined together by means of a hot melt adhesive (not shown).

In the case of the diaper 1A shown in FIG. 2, the pad 11 is joined to the first and second suspender members 19, 27 which are placed under extension in the transverse direction and these suspender members 19, 27 are joined to the pants member 2 of which the front and rear waist regions 38, 40 are placed under extension in the transverse direction.

To configurate the diaper 1A from a state as shown in FIG. 2, the diaper 1A may be folded back along a lateral center line L bisecting a longitudinal length of the diaper 1A with the topsheet 12 inside and the transversely opposite side edges 5 of the front and rear waist regions 38, 40 may be overlaid together and joined to each other together with the transversely opposite side edges 24, 32 of the first and second suspender members 19, 27.

In this diaper 1A, the first and second suspender members 19, 27 respectively have the side edges 24, 32 joined to the pants member 2 and respectively have the outer ends 23, 31 also joined to the pants member 2 at the joining zones 35. Such unique arrangement allows a wearer of the diaper 1A to smoothly wear the diaper 1A without any apprehension that the wearer's leg(s) might be caught by the first and/or the second suspender member(s) 19, 27 or erroneously inserted into a space between the pants member 2 and the first and/or the second suspender member(s) 19, 27.

The first and second suspender members 19, 27 are adapted to be fixed around the wearer's waist as this diaper 1A is worn so that the pad 11 connected to these suspender members 19, 27 may be maintained in close contact with the wearer's waist. In addition, the diaper 1A is characterized in that the first and second suspender members 19, 27 are only partially joined to the pants member 2 and movement transmission from the front and rear waist regions 38, 40 of the pants member 2 to the pad 11 can be effectively alleviated in comparison with the case in which the first and second suspender members 19, 27 are joined to the pants member 2 over the entire area. In other words, even if the front and rear waist regions 38, 40 of the pants member 2 slide down along the wearer's waist, there is no anxiety that the first and second suspender members 19, 27 and the pad 11 connected to these suspender members 19, 27 might slide down due to slipping down of the pad 11. In this way, the pad 11 is maintained in close contact with the wearer's body so that bodily discharges can be reliably absorbed and retained by the pad 11.

Figure 4:
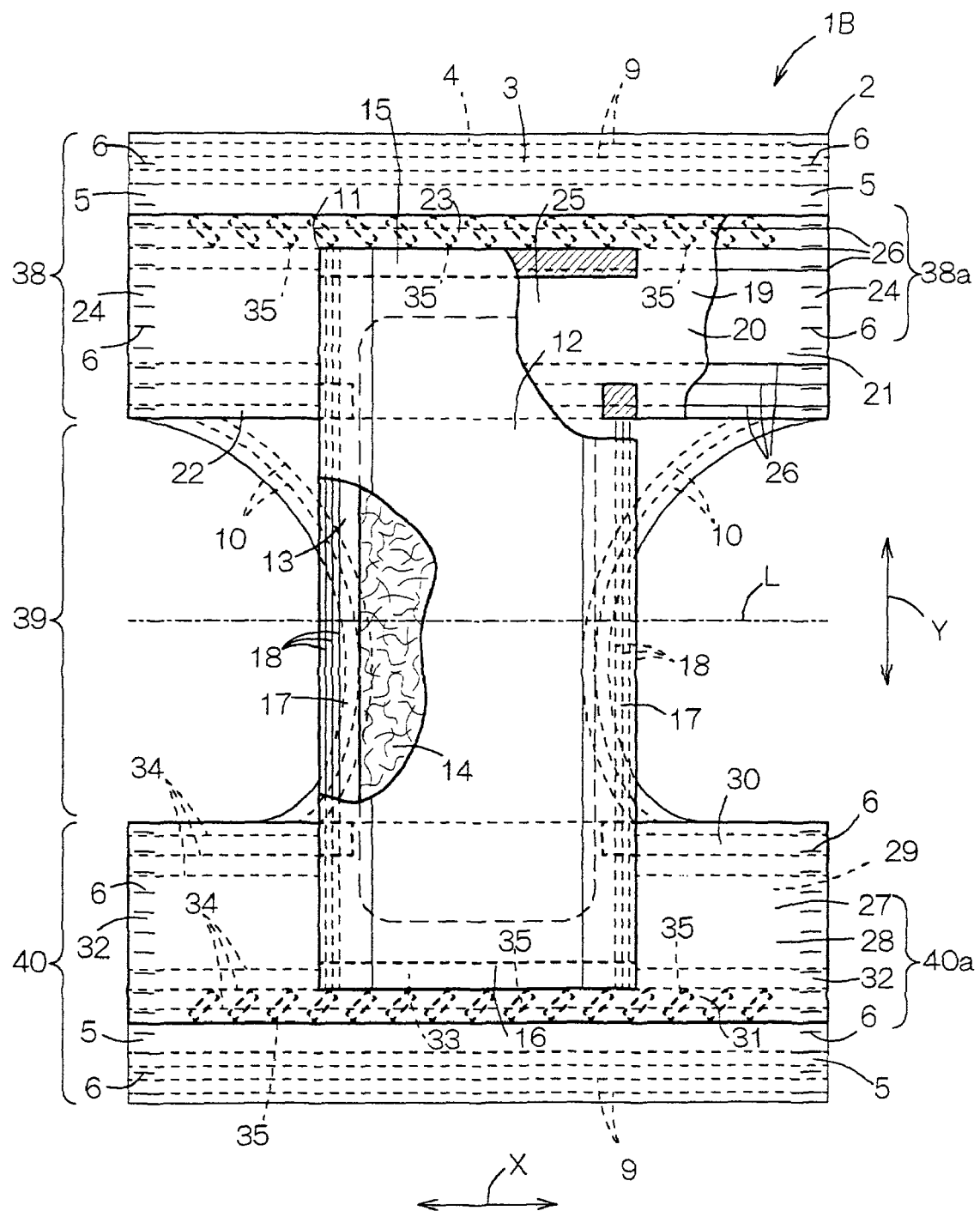
FIG. 4 is a partially cutaway plan view showing the diaper according to another embodiment of this invention as developed.

FIG. 4 is a partially cutaway plan view showing the diaper 1B according to another embodiment of this invention as it has been developed. Referring to FIG. 4, the pants member 2, the pad 11 and the first and second suspender members 19, 27 are under extension in the longitudinal direction as well as in the transverse direction.

This diaper 1B is similar to that shown in FIG. 1 in that the diaper 1B comprises the pants member 2, the body fluid absorbent pad 11 and the first and second suspender members 19, 27 lying between the pants member 2 and the pad 11 so as to connect them to each other. The diaper 1B is distinguished from the diaper 1A shown in FIG. 1 in that the outer ends 23, 31 of the first and second suspender members 19, 27 are joined to the front and rear waist regions 38, 40 of the pants member 2 at a plurality of the joining zones 35 arranged intermittently in the circumferential direction of the waist.

To configurate the diaper 1B from a state as shown in FIG. 4, the diaper 1B may be folded back along a lateral center line L bisecting a longitudinal length of the diaper 1B and the transversely opposite side edges 5 of the front and rear waist regions 38, 40 may be overlaid together and joined to each other together with the transversely opposite side edges 24, 32 of the first and second suspender members 19, 27.

In this diaper 1B, the number of intersections in the joining zones 35 formed by the outer ends 23, 31 of the first and second suspender members 19, 27 is much longer than that formed in the diaper 1A in FIG. 1 so that the diaper 1B can be more smoothly worn without any apprehension that the wearer's leg(s) might be caught by the first and/or the second suspender member(s) 19, 27 or erroneously inserted into a space between the pants member 2 and the first and/or the second suspender member(s) 19, 27.

These diapers 1A, 1B illustrated herein can utilize the elasticity of the first and second waist regions 38, 40 of the pants member 2 and the elasticity of the first and second suspender members 19, 27 to ensure that the diaper 1A, 1B can be tightly placed against the wearer's waist and be prevented from slipping down along the wearer's waist.

With these diapers 1A, 1B, the elastic members 18 attached to the side edges 17 of the pad 11 and the elastic members 26, 34 attached to the inner ends 22, 30 of the first and second suspender members 19, 27 present a substantially loop-like configuration as the front and rear waist regions 38, 40 are connected along the transversely opposite side edges 5 thereof. The elasticity of these elastic members 18, 26, 34 can be utilized to ensure that the diaper 1A, 1B can be tightly placed against the wearer's waist and possible leak of bodily discharges can be reliably prevented.

The topsheet 12 may be formed using a hydrophilic fibrous nonwoven fabric or finely apertured plastic film. The sheets 3, 4, 20, 21, 28, 29 and the backsheet 13 may be formed using a hydrophobic fibrous nonwoven fabric, liquid-impervious plastic film, two layers of hydrophobic fibrous nonwoven fabric placed upon each other, or a composite sheet consisting of hydrophobic fibrous nonwoven fabric and plastic film joined to this fibrous nonwoven fabric.

As a stock material for the sheets 3, 4, 20, 21, 28, 29 and the backsheet 13, forming the pants member 2 and the first and second suspender members 19, 27, it is also possible to use a composite nonwoven fabric consisting of a highly water-resistant fibrous nonwoven fabric made by melt blown process sandwiched by two layers of a spun join fibrous nonwoven fabric high in strength as well as in flexibility.

The nonwoven fabric may be selected from those made by spun lacing-, needle punching-, melt blowing-, thermal joining-, spun joining-, chemical joining and air-through processes. The component fiber for the nonwoven fabric may be selected from a group consisting of polyolefine-, polyester- and polyamide-based fibers, and core-sheath-type conjugated fiber or side-by-side-type conjugated fiber of polyethylene/polypropylene or polyethylene/polyester.

For these diapers 1A, 1B illustrated as the embodiments of this invention, it is possible to form the pants member 2 and first and second suspender members 19, 27 using elastically stretchable sheet. Such sheet may be selected from a group of materials consisting of an elastic and hydrophobic fibrous nonwoven fabric, an elastic and liquid-impervious plastic film, two layers of an elastic and hydrophobic fibrous nonwoven fabric placed upon each other and a composite sheet made of an elastic and hydrophobic fibrous nonwoven fabric and a liquid-impervious plastic film laminated upon each other.

The elastic fibrous nonwoven fabric may be selected from those made by melt blowing process and spun joining process. The component fiber for this elastic nonwoven fabric may be an elastic fiber obtained by a melt spinning thermoplastic elastomer resin. Alternatively, a hydrophobic fibrous nonwoven fabric made of a melt spun crimped fiber of thermoplastic synthetic resin such as polypropylene, polyethylene or polyester may be joined to at least one surface of hydrophobic fibrous nonwoven fabric made of a thermoplastic elastomer resin fiber to obtain a composite nonwoven fabric as the elastic fibrous nonwoven fabric useful for this invention.

The core 14 is a mixture of fluff pulp and super-absorbent polymer grains or a mixture of fluff pulp, super-absorbent polymer grains and thermoplastic synthetic resin fiber both compressed to a desired thickness. Preferably, the core 14 is entirely covered with tissue paper to prevent the polymer grains from falling off and/or to prevent the core 14 from deforming its shape. The polymer grains may be selected from a group of materials consisting of starch-, cellulose-and synthetic polymer-based grains.

Joining of the pad 11 to the first and second suspender members 19, 27 as well as joining of the pants member 2 to these first and second suspender members 19, 27 may be carried out using a hot melt adhesive or welding technique such as heat-sealing or ultrasonic sealing. Joining of the top- and backsheets 12, 13 and the core 14 as well as attachment of the elastic members 9, 10, 18, 26, 34 also may be carried out using a hot melt adhesive or welding technique such as heat-sealing or ultrasonic sealing.

The disposable diaper according to this invention is characterized in that the first and second suspender members are joined to the front and rear waist regions of the pants member not only along the side edges of these suspender members but also the outer ends of these suspender members at the joining zones arranged on the front and rear waist regions intermittently in the circumferential direction of the waist. Such unique arrangement allows the diaper to be smoothly worn without any anxiety that that wearer's leg(s) might be caught by the suspender member(s) or erroneously inserted into a space between the pants member and the suspender member(s).

In the case of the embodiment in which a plurality of elastic members extending in the circumferential direction of the waist are attached under extension to the front and rear waist regions of the pants member, the elasticity of the front and rear waist regions of the pants member and the elasticity of the first and second suspender members can be utilized to maintain the diaper in close contact with the wearer's waist and to prevent the diaper from slipping down along the wearer's waist.

What is claimed is:

1. A disposable diaper comprising:
   a pants member formed from two sheet members that are superimposed on one another, said pants member having an hourglass shape with front and rear waist regions that contain a plurality of elastic members positioned and extending between the two sheet members in a circumferential direction, transversely opposite side edge portions and a crotch region, wherein said transversely opposite side edge portions of said waist regions are overlaid and joined together so as to define a waist-hole and a pair of leg-holes;
   a body fluid absorbent pad lying inside said pants member and extending from said crotch region into said front and rear waist regions;
   a first elastically stretchable suspender member positioned between the pants member and the body fluid absorbent pad and connecting said pants member to the body fluid absorbent pad, said first suspender member extending in said front waist in a circumferential direction of the diaper between and to opposite side edge portions of the front waist region; and
   a second elastically stretchable suspender member positioned between the pants member and the body fluid absorbent pad and connecting said pants member to the body fluid absorbent pad, said second suspender member extending in said rear waist in a circumferential direction of the diaper between and to opposite side edge portions of the rear waist region, each of said first and second suspender members formed from two sheet members that are superposed on one another and being joined under extension in said circumferential direction of the diaper to said pants member, said pad having front and rear ends which extend across middle zones of said front and rear waist regions in a circumferential direction of said pants member and transversely opposite side edges which extend between said front and rear ends, said first and second suspender members respectively have lower edges which extend in said circumferential direction of the diaper bordering on said crotch region, upper edges which extend in said circumferential direction of the diaper in vicinity of said waist-hole and transversely opposite side edges which extend in said longitudinal direction between said lower and upper edges said front and rear ends of said pad being joined to said first and second suspender members in middle zones thereof as viewed in said circumferential direction of the diaper, said side edges of said first and second suspender members being joined to said front and rear waist regions along the side edges thereof as viewed in said circumferential direction of the diaper and said upper edges of said first and second suspender members being joined to said front and rear waist regions of said pants member along joining zones arranged intermittently in said circumferential direction of the diaper with at least one of said joining zones being immediately outside points at which the front and rear ends and the transversely side edges of the body fluid absorbent pad intersect each other.

2. The diaper according to claim 1, wherein said joining zones are formed on said upper edges of said first and second suspender members immediately outside intersections of the front and rear ends of the transversely opposite side edges of said pad.

3. The diaper according to claim 1, wherein said plurality of elastic members extending between the two sheet members of the pants member extend on the front and rear waist regions of said pants member in said circumferential direction of the waist and are spaced one from another in said longitudinal direction between said waist-hole and said leg-holes; wherein said first and second suspender members are attached to said front and rear waist regions being under extension in said circumferential direction of the waist; and wherein elastic members extending on the crotch region of said pants member in said circumferential direction of the legs are attached under extension to peripheral edges of said leg-holes.

4. The diaper according to claim 1, wherein said elastic members extending in said circumferential direction of the legs are attached under extension to said peripheral edges of said leg-holes.

5. The diaper according to claim 1, wherein said lower edges of said first and second suspender members are joined to the transversely side edges of the body fluid absorbent pad.

6. The diaper according to claim 1, wherein said first and second suspender members include elastic members that extend in the circumferential direction.

7. The diaper according to claim 6, wherein the elastic members of the first and second suspender members are positioned between the two sheet members of the first and second suspender members.

8. The diaper according to claim 7, wherein the elastic members of the first and second suspender members are located exclusively near the lower and upper edges of said first and second suspender members.

* * * * *